United States Patent
Liu et al.

(10) Patent No.: US 11,939,615 B2
(45) Date of Patent: Mar. 26, 2024

(54) PRODUCTION METHOD OF ENZYMATIC REACTION USING ADENOSINE INSTEAD OF ATP

(71) Applicant: ANHUI GSH BIO-TECH CO., LTD, Anhui (CN)

(72) Inventors: Shanshan Liu, Beijing (CN); Hui Liu, Beijing (CN); Wenwen Zhou, Beijing (CN); Yongfa Qin, Beijing (CN)

(73) Assignee: ANHUI GSH BIO-TECH CO., LTD., Anhui (CN)

( * ) Notice: Subject to any disclaimer, the term of this patent is extended or adjusted under 35 U.S.C. 154(b) by 1006 days.

(21) Appl. No.: 16/622,852

(22) PCT Filed: Jun. 6, 2018

(86) PCT No.: PCT/CN2018/090050
§ 371 (c)(1),
(2) Date: Dec. 13, 2019

(87) PCT Pub. No.: WO2018/228247
PCT Pub. Date: Dec. 20, 2018

(65) Prior Publication Data
US 2020/0131551 A1    Apr. 30, 2020

(30) Foreign Application Priority Data

Jun. 15, 2017  (CN) .......................... 201710452240.9
Jun. 15, 2017  (CN) .......................... 201710452799.1
Jun. 15, 2017  (CN) .......................... 201710453365.3

(51) Int. Cl.
*C12P 19/40*  (2006.01)
*C12N 9/12*   (2006.01)
(Continued)

(52) U.S. Cl.
CPC ............ *C12P 19/40* (2013.01); *C12N 9/1229* (2013.01); *C12N 9/16* (2013.01); *C12N 15/70* (2013.01);
(Continued)

(58) Field of Classification Search
None
See application file for complete search history.

(56) References Cited

U.S. PATENT DOCUMENTS 4,882,276 A * 11/1989 Imahori .................. C12P 13/20
                                              435/813
2005/0255568 A1* 11/2005 Bailey .................. C12N 9/1007
                                              435/193
(Continued)

FOREIGN PATENT DOCUMENTS

CN    102465162 A  †  5/2012
CN    102978267        3/2013
(Continued)

OTHER PUBLICATIONS

Baughn ("Large-scale Enzyme Catalyzed Synthesis of ATP from Adenosine and Acetyl Phosphate Regeneration of ATP from AMP" J. Am. Chem. Soc., 100, 304 (1978) (Year: 1978).*
(Continued)

*Primary Examiner* — Robert J Yamasaki
*Assistant Examiner* — Charles Zoltan Constantine
(74) *Attorney, Agent, or Firm* — BOOTH UDALL FULLER, PLC; Pacer K. Udall

(57) ABSTRACT

The present invention discloses a production method of enzymatic reaction using adenosine instead of ATP. The method comprises the following steps: (1) adding ATP regeneration enzyme, AK enzyme and adenosine in proportion to carry out an enzymatic reaction in an enzymatic reaction system; (2) separating the ATP regeneration enzyme and AK enzyme by either directly separating ATP regeneration enzyme and AK enzyme immobilized in a reaction tank or separating free ATP regeneration enzyme and AK enzyme by an ultrafiltration membrane in a filter; and (3) separating and purifying the filtrate of step (2) to obtain a product. The disclosed method provides: greatly reduced industrial production costs; faster reaction rate; stable enzyme recovery system that is energy efficient and environmentally friendly; and capability of reusing the byproducts or collecting them for the production of ATP.

4 Claims, 3 Drawing Sheets
Specification includes a Sequence Listing.

(51) Int. Cl.
  *C12N 9/16* (2006.01)
  *C12N 15/70* (2006.01)
(52) U.S. Cl.
  CPC ............ *C12Y 207/04001* (2013.01); *C12Y 207/04003* (2013.01); *C12Y 301/03004* (2013.01)

(56) References Cited

U.S. PATENT DOCUMENTS

2006/0134739 A1* 6/2006 Chatterjee ............... C12P 19/34 435/252.33
2020/0199641 A1† 6/2020 Liu

FOREIGN PATENT DOCUMENTS

| CN | 105219823 A † | 1/2016 |
| CN | 105603028 A | 5/2016 |
| CN | 105647996 | 6/2016 |
| CN | 105861598 | 8/2016 |
| CN | 106191170 A † | 12/2016 |

OTHER PUBLICATIONS

Shiba ("Polyphosphate:AMP Phosphotransferase as a Polyphosphate-Dependent Nucleoside Monophosphate Kinase in Acinetobacter johnsonii 210A" Journal of Bacteriology, 2005, 1859-1865) (Year: 2005).*

Wikipedia ("S-Adenosylmethionine synthetase enzyme" webcapture from Apr. 12, 2016 provided by WayBack Machine, available at https://web.archive.org/web/20160412064050/https://en.wikipedia.org/wiki/S-Adenosylmethionine_s (Year: 2016).*

Fox, C &EN, pp. 15-16, Jun. 5, 1978.†

Maj, Biochimica et BioPhysica Acta, pp. 33-42, 2000.†

\* cited by examiner
† cited by third party

PRODUCTION METHOD OF ENZYMATIC REACTION USING ADENOSINE INSTEAD OF ATP

CROSS REFERENCE TO RELATED APPLICATIONS

This application is the U.S. National Stage of International Application No. PCT/CN2018/090050, filed Jun. 6, 2018, which claims the benefit of Chinese Patent Application Nos. CN201710453365.3, CN201710452240.9 and CN201710452799.1, filed Jun. 15, 2017, the contents of each of which are incorporated herein by reference in their entireties.

TECHNICAL FIELD

The present invention relates to the field of biotechnology, in particular to a production method of enzymatic reaction using adenosine instead of ATP.

BACKGROUND ART

Adenosine triphosphate (ATP) consists of one adenosine and three phosphate groups with a molecular weight of 507 and a molecular formula of $C_{10}H_{16}N_5O_{13}P_3$. It is a converter and reservoir of bioenergy and plays an irreplaceable role in an enzymatic reaction of utilizing and converting energy.

Due to the current high cost of ATP, the direct use of ATP in industrial production for the enzymatic reaction has little benefit. Therefore, it is the current research direction of industrial production using ATP by investing a small amount of ATP in the reaction production, and establishing a stable and effective ATP regeneration system to recycle ATP in a reaction process.

A common method for ATP regeneration in the industry is to use the glycolytic pathway by yeast to regenerate ATP by substrate level phosphorylation. Many enzymes are involved in the catalytic reaction in this method, the reaction process is complicated, the reaction process is difficult to control, and a large difference in the quality of products exists from batch to batch. At the same time, the quality of yeast enzymes is often of great difference due to different manufacturers, batches, and even seasons. In addition, the addition of a large amount of yeast cell enzyme solution is required in the reaction process, and many impurities such as proteins and pigments are brought in, thereby causing certain difficulties in the later purification. In recent years, the focus of research on ATP regeneration has shifted to the use of a single enzyme or a simpler enzyme system to achieve a high-efficiency and stable regeneration effect. Among them, enzymes such as acetate kinase, ammonia kinase and pyruvate kinase and the like, can effectively regenerate ATP. However, the substrates utilized by these enzymes are expensive, for example, the phosphoenolpyruvic acid utilized by pyruvate kinase; and the by-products produced have certain biotoxicity and pollution, for example, the products of acetate kinase and ammonia kinase-catalyzed reactions are acetic acid and ammonia, respectively, therefore they are difficult to be used in large quantities in industrial production.

Patent CN201610268246.6 utilizes polyphosphoric acid or its salt as a phosphoric acid and energy donor, and uses a reasonable combination of three "ATP regeneration enzymes" such as polyphosphate kinase (PPK, EC 2.7.4.1), adenylate kinase (ADK, EC 2.7.4.3) and polyphosphate: AMP phosphotransferase (PAP, EC 2.7.4.-, which is reported in the literature as a class of PPK enzymes, but the classification of this enzyme is not well defined by IUBMB) to regenerate ATP, which is also applied to a variety of enzymatic reactions requiring ATP. The method has the advantages of using relatively cheap substrate, and having less product contamination, and the method is suitable for industrial production. However, the use of this method still requires the addition of a certain amount of ATP for enzymatic reaction.

SUMMARY OF THE INVENTION

The present invention provides a production method of enzymatic reaction using adenosine instead of ATP, which can further reduce the production cost, that is, adding adenosine kinase (AK, EC 2.7.1.20) in the original reaction system containing ATP regeneration enzyme. The ATP regeneration enzyme can catalyze adenosine to produce adenosine monophosphate (AMP), and in combination with the above other ATP regeneration enzymes, no ATP can be used, and the enzymatic reaction can be performed with only adding a small amount of adenosine, and this is a major innovation in the field.

The technical problem to be solved by the present invention is achieved by the following technical solutions:

A production method of enzymatic reaction using adenosine instead of ATP is provided, and the enzymatic reaction is an enzymatic reaction requiring ATP, and includes the following steps:

(1) in the enzymatic reaction system, adding ATP regeneration enzyme, AK enzyme and adenosine in proportion to carry out the enzymatic reaction:

obtaining the ATP regeneration enzyme and AK enzyme by genetic engineering, fermentation, and purification, or obtaining the ATP regeneration enzyme and AK enzyme by other methods such as natural extraction and the like. The ATP regeneration enzyme and the AK enzyme may be prepared into an enzyme solution or a dry powder in the form of a free enzyme; or may be further immobilized on an immobilized carrier to obtain an immobilized ATP regeneration enzyme and an AK enzyme.

In the enzymatic reaction system, the enzymatic reaction is carried out by adding ATP regeneration enzyme and AK enzyme in proportion and adding adenosine instead of ATP. Wherein, the reaction system is an aqueous solution containing one or two of adenosine, polyphosphoric acid or a salt thereof, magnesium ions and manganese ions. In addition, the reaction system may further include one or more of potassium ions, sodium ions, ammonium ions, and one or more of Tris and phosphate ions. The above substrates, enzymes and various salts may be added to the reaction system in one portion, or may be fed in batches according to the industrial production process in the present invention.

(2) directly separating the immobilized ATP regeneration enzyme and AK enzyme in the reaction tank, and separating the free ATP regeneration enzyme and AK enzyme by an ultrafiltration membrane in a filter:

directly separating the immobilized ATP regeneration enzyme and AK enzyme in the reaction tank, wherein the above separation can be carried out by a filter bag or directly in a reaction column. Alternatively, the free ATP regeneration enzyme and AK enzyme are separated by an ultrafiltration membrane in a filter. Wherein, the filter has a feed port, a discharge port and a reflux port, and an ultrafiltration membrane with a cut-off disposed therein. The retentate after filtration is the recovered enzyme solution, and the filtrate is the reaction solution containing the product without enzymes.

(3) separating and purifying the filtrate of step (2) to obtain a product.

Preferably, in the above technical solution, the method further includes the following steps:

(4) recovering the ATP regeneration enzyme and the AK enzyme, and recycling in step (1) for the reaction; and (5) separating a small amount of ATP, adenosine diphosphate (ADP) or AMP produced in the reaction by filtration or ion exchange to produce ATP; or recovering the ATP, ADP or AMP and recycling in step (1) for reaction.

Preferably, in the above technical solution, In step (1), the ATP regeneration enzyme and the AK enzyme are immobilized or free enzymes; the concentration of AK enzyme is 0.01-8000 U/L, wherein the enzyme activity is defined as 1 unit (U) by the completed conversion of 1 μM substrate within 1 minute; ATP regeneration enzyme is a combination of any two or three of polyphosphate kinase (PPK), adenylate kinase (ADK) and polyphosphate: AMP phosphotransferase (PAP), that is, the combination of PPK and ADK, or the combination of ADK and PAP, or the combination of PPK and PAP, or the combination of PPK, ADK and PAP is used; and by the addition amount of enzyme, the concentration of PPK enzyme is 0.01-5000 U/L, the concentration of ADK enzyme is 0.01-5000 U/L, and the concentration of PAP enzyme is 0.01-5000 U/L. When three regeneration enzymes are applied, the optimal ratio is as follows: PPK:ADK:PAP=1:1:1. The above ATP regeneration enzyme and AK enzyme may be derived from any organism or an enzyme that has been artificially engineered to have the same catalytic function.

Preferably, in the above technical solution, the reaction conditions in step (1) are as follows:

the reaction temperature is 25-55° C., preferably the temperature is 30-50° C.;

the reaction pH is 5-10, preferably the pH is 6-9;

the reaction system includes: a combination of one or two of adenosine; polyphosphoric acid or a salt thereof; magnesium ions and manganese ions; and in the enzymatic reaction system, the ATP regeneration enzyme and the AK enzyme are added in proportion to carry out the enzymatic reaction.

Preferably, in the above technical solution, the reaction in step (1) further includes:

a combination of one or more of ammonium ions, potassium ions or sodium ions; and a combination of one or two of Tris or phosphate ions; wherein the concentration of potassium ion is 0.01-0.5 M; the concentration of sodium ion is 0.01-0.5 M; the concentration of ammonium ion is 0.01-0.3 M; the concentration of Tris is 0.01-0.1 M; and the concentration of phosphate is 0.01-0.1 M.

Preferably, in the above technical solution, the concentration of adenosine in step (1) is 0.01-50 g/L, preferably 0.01-5 g/L; the concentration of polyphosphoric acid or a salt thereof is 0.01-0.3 M; and the concentration of magnesium ion is 0.01-0.2 M; and the concentration of manganese ion is 0.005-0.15 M.

Preferably, in the above technical solution, the magnesium ion is selected from the group consisting of one or more of magnesium chloride, magnesium sulfate, magnesium sulfite and magnesium nitrate; and the manganese ion is selected from the group consisting of one or more of manganese chloride and manganese sulfate; the potassium ion is selected from the group consisting of one or more of potassium chloride, potassium sulfate, potassium nitrate, potassium hydroxide, potassium sulfite, potassium carbonate, potassium bicarbonate, potassium acetate, dipotassium hydrogen phosphate, potassium dihydrogen phosphate, and potassium citrate; the sodium ion is selected from the group consisting of one or more of sodium chloride, sodium sulfate, sodium nitrate, sodium hydroxide, sodium sulfite, sodium carbonate, sodium bicarbonate, sodium acetate, disodium hydrogen phosphate, sodium dihydrogen phosphate, and sodium citrate; the ammonium ion is selected from the group consisting of one or more of ammonium chloride, ammonium sulfate, ammonium nitrate, aqueous ammonia, ammonium carbonate, ammonium bicarbonate, diammonium hydrogen phosphate, ammonium dihydrogen phosphate, and ammonium acetate; and the polyphosphoric acid or a salt thereof is selected from the group consisting of one or more of sodium polyphosphate, potassium polyphosphate, and ammonium polyphosphate.

Preferably, in the above technical solution, in step (2), the ATP regeneration enzyme and AK enzyme are immobilized on the immobilization carrier by the following mode: adsorption, encapsulation, covalent bonding, crosslinking or a combination thereof; and the immobilization carrier is selected from one or more of a polymer carrier, an inorganic carrier, and a magnetic polymer microsphere carrier. Wherein, the polymer carrier is selected from the group consisting of cellulose, glucose gel, agarose, polyacrylamide, polyamino acid, polystyrene, polyacrylic acid, sodium alginate, chitosan, starch, polyvinyl alcohol, gelatin, carrageenan, nylon or synthetic high polymer and the like; and the inorganic carrier is selected from the group consisting of porous glass, silica, silica gel, activated carbon or diatomaceous earth.

Preferably, in the above technical solution, the ultrafiltration membrane is selected from the group consisting of a cellulose acetate membrane, a polysulfone membrane, a polyacrylonitrile membrane, a polyvinyl chloride membrane, a polyvinylidene fluoride membrane, a polyamide membrane or a ceramic membrane.

A use of a production method of enzymatic reaction using adenosine instead of ATP is provided, and the method is used for a variety of enzymatic reactions requiring ATP for the synthesis of substances and cell-free protein expression.

Preferably, in the above technical solution, the enzymatic reaction requiring ATP is an enzymatic reaction in which a transferase (EC 2.7) for transferring a phosphate group is involved, an enzymatic reaction in which a part of the ligase is involved, and an enzymatic reaction in which a part of adenosyltransferase is involved. The enzymatic reaction in which a transferase (EC 2.7) for transferring a phosphate group is involved, for example, the synthesis reaction of substances of creatine phosphate, arginine phosphate, hexose 6-phosphate, fructose 1,6-phosphate, glycerol 3-phosphate, oxidized form of coenzyme II, CT(D)P, GT(D)P, UT(D)P and the like; the enzymatic reaction in which a part of the ligase (EC 6) is involved, for example, the synthesis reaction of substances of glutathione, acetyl-coenzyme A, carnosine, enteromycin, glutamine, L-theanine, cyanophycin and D-alanyl alanine and the like; and the enzymatic reaction in which a part of adenosyltransferase is involved, for example: synthesis reaction of S-adenosylmethionine.

The catalytic enzymes and substrates required for the above enzymatic synthesis reactions are shown in Table 1 below. The catalytic enzymes listed in Table 1 can be derived from any organisms or are artificially engineered to have the same catalytic function and are commercially available.

TABLE 1

Catalytic Enzymes and Substrates for Enzymatic Reaction According to the Present Invention

| Names of substance | Catalytic enzymes | Substrates |
|---|---|---|
| Creatine phosphate | Creatine kinase (EC2.7.3.2) | Creatine |
| Arginine phosphate | Arginine kinase (EC2.7.3.3) | Arginine |
| Hexose 6-phosphate | Hexokinase (EC2.7.1.1) | Hexose |
| Fructose 1,6-diphosphate | Fructokinase (EC2.7.1.4), phosphofructokinase (EC2.7.1.11) | Fructose |
| Glycerol 3-phosphate | Glycerol kinase (EC2.7.1.30) | Glycerol |
| Oxidized form of coenzyme II (NADP$^+$) | NAD$^+$ kinase (EC2.7.1.23) | NAD$^+$ |
| CT(D)P | Nucleotide kinase (EC2.7.4.4)/ ribonucleoside diphosphate kinase (EC2.7.4.6) | CD(M)P |
| UT(D)P | UMP kinase (EC2.7.4.22)/ ribonucleoside diphosphate kinase (EC2.7.4.6) | UD(M)P |
| GT(D)P | GMP kinase (EC2.7.4.8)/ ribonucleoside diphosphate kinase (EC2.7.4.6) | GD(M)P |
| Glutathione | Bifunctional glutathione synthetase (EC6.3.2.2/ EC6.3.2.3) | L-glutamic acid, L-cysteine, glycine |
| Acetyl coenzyme A | Acetyl coenzyme A synthetase (EC6.1.1.1) | Acetic acid, coenzyme A |
| Carnosine | Carnosine synthetase (EC6.3.2.11) | L-histidine, P-alanine |
| Enterobactin | Enterobactin synthetase (EC6.3.2.14) | Methyl 2,3-dihydroxybenzoate, L-serine |
| Glutamine | Glutamine synthetase (EC6.3.1.2) | Glutamate, ammonia |
| L-theanine | Theanine synthetase (EC6.3.1.6) | Sodium glutamate, ethylamine |
| Cyanophycin | Cyanophycin synthetase (EC6.3.2.29) | L-arginine, L-aspartate |
| D-alanyl alanine | D-alanylalanine synthetase (EC6.3.2.4) | D-alanine |
| S-adenosyl-methionine | Methionine adenosylytransferase (EC2.5.1.6) | Adenosine, L-methionine |

Preferably, in the above technical solution, the method is applied to a cell-free protein expression technique.

The cell-free protein expression technology refers to protein synthesis in vitro of cell lysates containing components necessary for protein synthesis (ribosomes, transfer RNA, initiation/extension/termination factors, ATP, magnesium ions, potassium ions and the like).

The above technical solutions of the present invention have the following beneficial effects:

1) The use of adenosine instead of ATP or AMP greatly reduces the cost of industrial production. The price of adenosine is only about 10% of ATP or 30% of AMP, adenosine is cheaper and has abundant sources, and its usage amount in the reaction can be optimized to be less than 10% of that of the original ATP.

2) a stable enzyme recycling system has been established, and both the immobilized enzyme and the free enzyme can be recycled during the whole reaction process, and it is low in cost, energy saving and environment friendly after being applied to large-scale continuous production; and 3) a small amount of by-products ATP, ADP and AMP produced can be either directly used for the cyclic reaction, or for the production of ATP, or intensively purified by filtration, ion exchange, etc., therefore, the operation is simple, and the purified product can be used as an additional product, thereby having certain economic benefits.

DETAILED DESCRIPTION OF THE EMBODIMENTS

The specific examples of the present invention are described in detail below, in order to further understand the present invention. The various materials used in the following examples and comparative examples of the present invention can be obtained commercially, unless otherwise specified.

Example 1 Preparation of Crude Enzyme

The ATP regeneration enzyme and AK enzyme in the method of the present invention are commercially available, or are enzymes that have been artificially engineered to have the same catalytic function.

The preparation process of the enzyme is as follows:

Primers were designed based on the gene sequences of each of PPK enzyme, ADK enzyme, PAP enzyme and AK enzyme, and the gene fragments were amplified by PCR and ligated to the pET22b plasmid (commercially available), respectively, and transferred to *E. coli* BL21 (DE3) strain (commercially available) after sequencing with correct result.

The transformed *E. coli* BL21 (DE3) monoclone was inoculated into LB medium, and after incubation to logarithmic phase, 1 mM isopropyl-β-D-thiogalactopyranoside (IPTG) was added for induction. The bacteria were harvested after 5 hours of induction, and the high expression strains were screened using sodium dodecyl sulfate-polyacrylamide gel electrophoresis (SDS-PAGE).

The selected high expression strains were inoculated into the seed culture medium under sterile conditions, cultured until reached to the logarithmic growth phase, and then amplificated and finally transferred into a fermenter containing 500 L of fermentation medium. After the OD600 value reached 20-30, 1 mM IPTG was added for 5 hours of induction, and the bacteria were collected by centrifugation.

The composition of LB medium was: 1% peptone, 0.5% yeast extract powder and 1% sodium chloride; the composition of the seed medium was: 1% peptone, 0.5% yeast extract powder and 1% sodium chloride; and the composition of the fermentation medium was: 1% peptone 0.5% yeast extract powder, 1% sodium chloride, 5% disodium hydrogen phosphate, 1% sodium dihydrogen phosphate, 0.01% magnesium sulfate and 1% glycerol.

Figure 1:
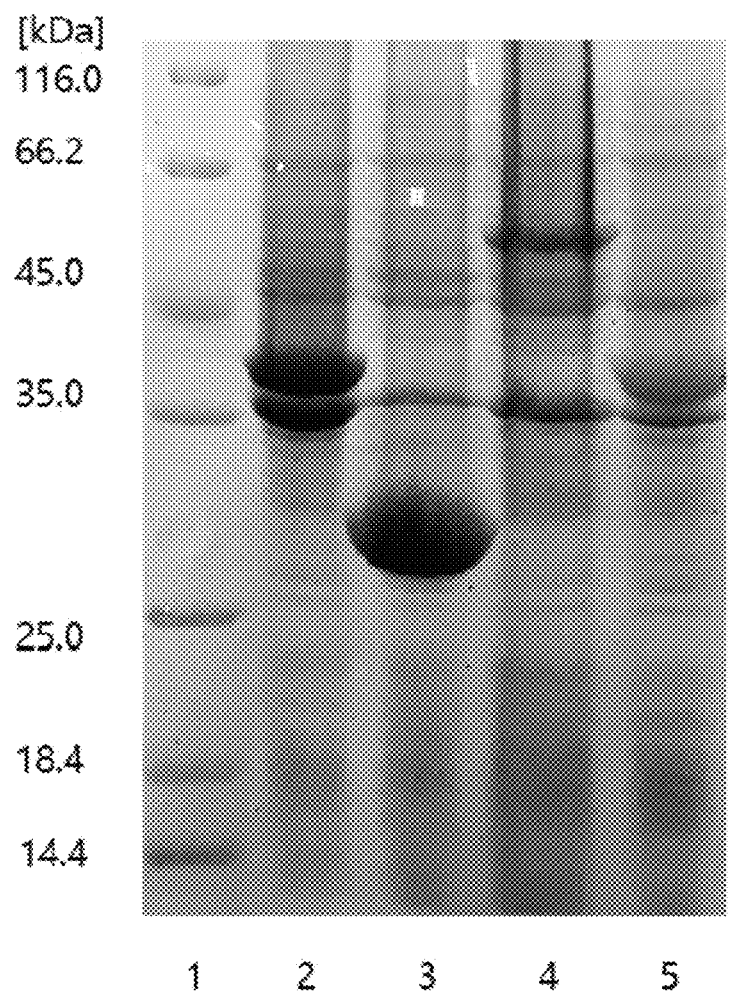
FIG. 1 is an SDS-PAGE diagram of *Escherichia coli* expressed PPK enzyme, ADK enzyme, PAP enzyme and AK enzyme.

FIG. 1 is an SDS-PAGE diagram of *Escherichia coli* expressed PPK enzyme, ADK enzyme, PAP enzyme and AK enzyme. As shown in FIG. 1: Lane 1 was the protein marker 14.4-116 kDa (commercially available); Lane 2 was the PPK enzyme, 40 kDa; Lane 3 was the ADK enzyme, 25 kDa; Lane 4 was a PAP enzyme, 55 kDa; and Lane 5 was an AK enzyme, 40 kDa.

After the harvested bacteria were homogenized and crushed under ultrasound or high pressure, the supernatant was collected by centrifugation. The crude enzyme was obtained by precipitation and filtration methods.

In this example, since the crude enzyme solution simultaneously contained a trace amount of ATP, the reaction can be started without additional ATP, and the operation was more convenient.

Example 2 Production of Creatine Phosphate by an Enzymatic Method

Figure 2:
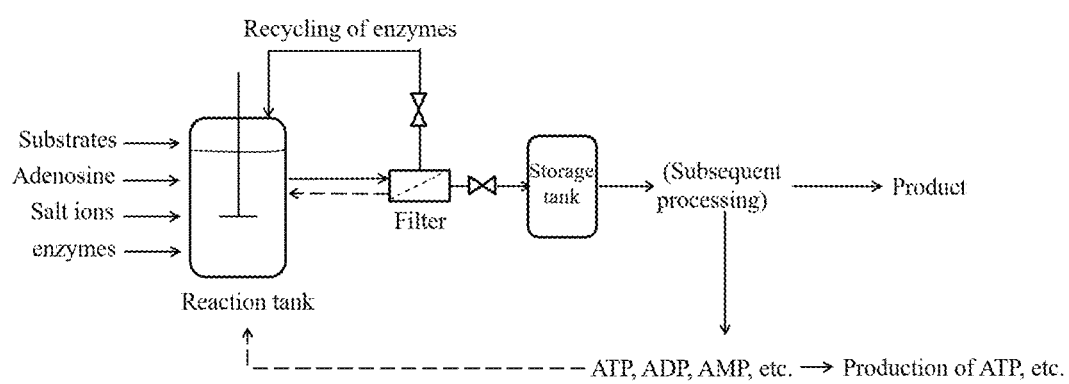
FIG. 2 is a flow chart showing the reaction process using the free enzyme according to the present invention.

FIG. 2 is a flow chart showing the reaction process using the free enzyme according to the present invention. As shown in FIG. 2, the operating steps for preparing creatine phosphate by an enzymatic method are as follows:

(1) Reaction of Synthesizing Creatine Phosphate in a Reaction Tank:

in the reaction tank, 100 L of the reaction system was a solution containing substrate 2.0 kg of creatine, and 0.2 kg of adenosine, 1.8 kg of sodium polyphosphate, 0.4 kg of potassium chloride, 0.5 kg of magnesium chloride hexahydrate, and 0.3 kg of disodium hydrogen phosphate, and the solution was uniformly stirred when formulated to prevent precipitation. The pH was adjusted to 7.0, and creatine kinase 1000 U/L, PPK enzyme 500 U/L, ADK enzyme 500 U/L, and AK enzyme 500 U/L were added to the reaction system to start the reaction. The pH value was controlled to 7.0 during the reaction and the temperature was 35° C.

Figure 4:
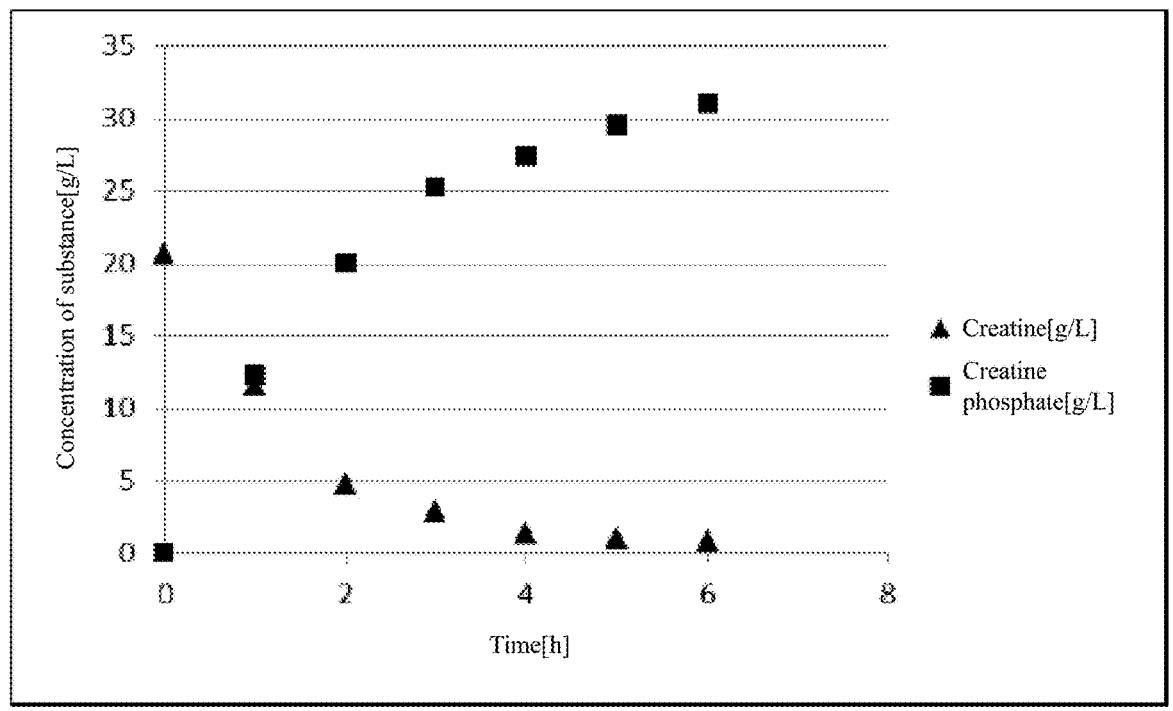
FIG. 4 is a graph showing the residual amount of creatine and the production amount of creatine phosphate detected by high performance liquid chromatography.

FIG. 4 is a graph showing the residual amount of creatine and the production amount of creatine phosphate detected by high performance liquid chromatography. As shown in FIG. 4, the residual amount of creatine and the production amount of creatine phosphate were detected by high performance liquid chromatography (HPLC) every 1 hour, and after 6 hours of reaction, the production amount of creatine phosphate was 30 g/L. The detection conditions of HPLC were as follows: Kromasil C18 chromatographic column (purchased from AKZO NOBEL) (150×4.6 mm), detection wavelength of 210 nm, and detection temperature of 25° C., the detection flow rate of 1 ml/min, and a mobile phase of an aqueous solution (pH 6.6) containing 0.2% potassium dihydrogen phosphate, 0.1% tetrabutylammonium hydroxide, and 5% acetonitrile.

(2) Separation of Creatine Kinase, ATP Regeneration Enzyme and AK Enzyme in a Filter:

the reaction solution in the reaction system of step (1) was passed through a filter to separate the creatine kinase, ATP regeneration enzyme and AK enzyme by an ultrafiltration method, and a membrane package (purchased from Pall Corporation, with a molecular weight cut off of 20 kDa) was placed in the filter, and the filtrate was a reaction solution containing creatine phosphate, ATP, ADP, AMP and salts and the like after the enzyme was separated, and the filtrate can be further purified by ion exchange chromatography and the like.

The recovered creatine kinase, PPK enzyme, ADK enzyme and AK enzyme were detected to have an activity which is reduced by 5%-20% compared with that before the reaction, and can be used again for the reaction in step (1) after the corresponding new enzyme was added.

Example 3 Production of Glutathione by an Enzymatic Method

As shown in FIG. 2, the operating steps for preparing glutathione (GSH) by an enzymatic method are as follows:

(1) Generation of GSH in the Reaction Tank:

in the reaction tank, 100 L of the reaction system was a solution containing substrate 2.5 kg of glutamic acid, 2.5 kg of cysteine and 1.5 kg of glycine, 0.3 kg of adenosine, and 2.5 kg of sodium hexametaphosphate, 0.2 kg of ammonium sulfate, 0.3 kg of sodium chloride, 0.5 kg of magnesium chloride hexahydrate, 0.1 kg of manganese chloride monohydrate and 0.5 kg of disodium hydrogen phosphate, and the solution was uniformly stirred when formulated to prevent precipitation. The pH was adjusted to 7.0, and GshF enzyme 800 U/L, PPK enzyme 500 U/L, ADK enzyme 500 U/L, PAP enzyme 200 U/L and AK enzyme 600 U/L were added to the reaction system to start the reaction, and the enzymes added were all crude enzyme solutions. The pH value was controlled to 7.0 during the reaction and the temperature was 37° C.

After 5 hours of reaction, the production amount of glutathione was detected by high performance liquid chromatography (HPLC) to be 35 g/L. The detection conditions of HPLC were as follows: Kromasil C18 chromatographic column (purchased from AKZO NOBEL) (150×4.6 mm), detection wavelength of 210 nm, and detection temperature of 25° C. The mobile phase was an aqueous solution containing 6.8 g/L potassium dihydrogen phosphate, 2.0 g/L sodium heptanesulfonate and 3% methanol, and the pH is 3.0.

(2) Separation of the Enzyme in the Filter:

the reaction solution of step (1) was passed through a filter to separate the mixed enzyme by an ultrafiltration method, and a membrane package (purchased from Pall Corporation, with a molecular weight cut off of 20 kDa) was placed in the filter, and the filtrate was a reaction solution containing GSH, ATP, ADP, AMP and salts and the like after the enzyme was separated, and the filtrate can be further purified by ion exchange chromatography and the like. The enzyme separated in step (2) was added to the reaction tank through a reflux port of the filter, and a new enzyme having a concentration of 5-10% of the original enzyme was added for the reaction. The reaction solution was formulated in the same manner as in the above step (1).

The continuous reaction for producing GSH was carried out under the conditions of a pH 7.0 at 37° C.; after 5 hours, the production amount of GSH detected by HPLC was 32 g/L.

Example 4 Production of Glutathione by an Enzymatic Method

As shown in FIG. 2, the operating steps for preparing glutathione (GSH) by an enzymatic method are as follows:

(1) Generation of GSH in the Reaction Tank:

In the reaction tank, 100 L of the reaction system was a solution containing substrate 2.0 kg of glutamic acid, 2.0 kg of cysteine hydrochloride and 2.0 kg of glycine, 0.2 kg of adenosine, and 1.5 kg of sodium hexametaphosphate, 0.2 kg of ammonium chloride, 0.2 kg of potassium chloride, 0.8 kg of magnesium chloride hexahydrate, and 0.3 kg of Tris, and the solution was uniformly stirred when formulated to prevent precipitation. The pH was adjusted to 7.4, and GshF enzyme 1000 U/L, PPK enzyme 300 U/L, ADK enzyme 300 U/L, and AK enzyme 500 U/L were added to the reaction system to start the reaction, and the enzymes added were all crude enzyme solutions. The pH value was controlled to 7.4 during the reaction and the temperature was 40° C.

After 6 hours of reaction, the production amount of glutathione was detected by high performance liquid chromatography (HPLC) to be 30 g/L. The HPLC detection conditions were the same as those in step (1) of Example 3.

(2) Separation of the Enzyme in the Filter:

the reaction solution of step (1) was passed through a filter to separate the mixed enzyme by an ultrafiltration method, and a membrane package (purchased from Pall Corporation, with a molecular weight cut off of 20 kDa) was placed in the filter, and the filtrate was a reaction solution after the enzyme was separated.

(3) Separation Products GSH and Other Substances:

the pH of the filtrate was adjusted to 3.0 with hydrochloric acid, and passed through the D001 macroporous strong acid styrene cation exchange resin in the ion exchange column. The GSH, a part of amino acids and cations in the solution were adsorbed, and the through-liquid mainly contained ATP, ADP and AMP.

The GSH on the cation exchange resin was eluted with a gradient of 0-0.8 M NaCl, and the production amount of GSH was 2.7 kg with a yield of 90%.

(4) A continuous reaction for generating GSH in the reaction tank, that is, a continuous reaction of step (1):

the enzyme separated in step (2) was added to the reaction tank through a reflux port of the filter, and a new enzyme having a concentration of 5-10% of the original enzyme was added for the reaction. The ion exchanged through-liquid in step (3) was added to the reaction tank for solution formulation, and the formulation method of the reaction solution was the same as the above step (1), and the addition amount of adenosine was reduced to 0.03 kg.

The continuous reaction for producing GSH was carried out under the conditions of a pH 7.4 at 40° C.; after 6 hours, the production amount of GSH detected by HPLC was 30 g/L. The HPLC detection conditions were the same as those in step (1) of Example 3. In this step, the enzyme was recycled, and by-products such as ATP and the like generated in the previous cycle were recycled.

Example 5 Production of S-Adenosylmethionine by an Enzymatic Method

As shown in FIG. 2, a process flow diagram for the preparation of S-adenosylmethionine (SAM) according to the present invention uses a free enzyme to prepare an SAM according to the following steps:

(1) Generation of SAM in the Reaction Tank:

in the reaction tank, 100 L of the reaction system was a solution containing substrate 1.2 kg of methionine, 2.5 kg of adenosine, and 2.0 kg of sodium hexametaphosphate, 0.27 kg of ammonium chloride, 1.0 kg of magnesium chloride hexahydrate, and 0.8 kg of potassium dihydrogen phosphate, and the solution was uniformly stirred when formulated to prevent precipitation. The pH was adjusted to 7.2, and MAT enzyme 400 U/L, PPK enzyme 200 U/L, ADK enzyme 200 U/L, and AK enzyme 400 U/L were added to the reaction system to start the reaction, and the enzymes added were all crude enzyme solutions. The pH value was controlled to 7.2 during the reaction and the temperature was 35° C.

After 6 hours of reaction, the production amount of SAM was detected by high performance liquid chromatography (HPLC) to be 27 g/L. The detection conditions of HPLC were as follows: Kromasil C18 chromatographic column (the same as that in Example 2), detection wavelength of 260 nm, and detection temperature of 25° C. The mobile phase was an aqueous solution containing 1% glacial acetic acid, 2.0 g/L sodium heptanesulfonate and 10% methanol, and the pH is 4.0.

(2) Separation of the Enzyme in the Filter:

The reaction solution of the step (1) was passed through a filter to separate the mixed enzyme by an ultrafiltration method, and a membrane package (purchased from Pall Corporation, with a molecular weight cut off of 20 kDa) was placed in the filter, and the filtrate was a reaction solution containing SAM, ATP, ADP, AMP and salts and the like after the enzyme was separated, and the filtrate can be further purified by ion exchange chromatography and the like. The enzyme separated in step (2) was added to the reaction tank through a reflux port of the filter, and a new enzyme having a concentration of 10% of the original enzyme was added for the reaction. The reaction solution was formulated in the same manner as in the above step (1).

The continuous reaction for producing SAM was carried out under the conditions of a pH 7.2 at 35° C.; after 6 hours, the production amount of SAM detected by HPLC was 27 g/L. The HPLC detection conditions were the same as those in the above step (1). In this step, the enzyme was recycled.

Figure 3:
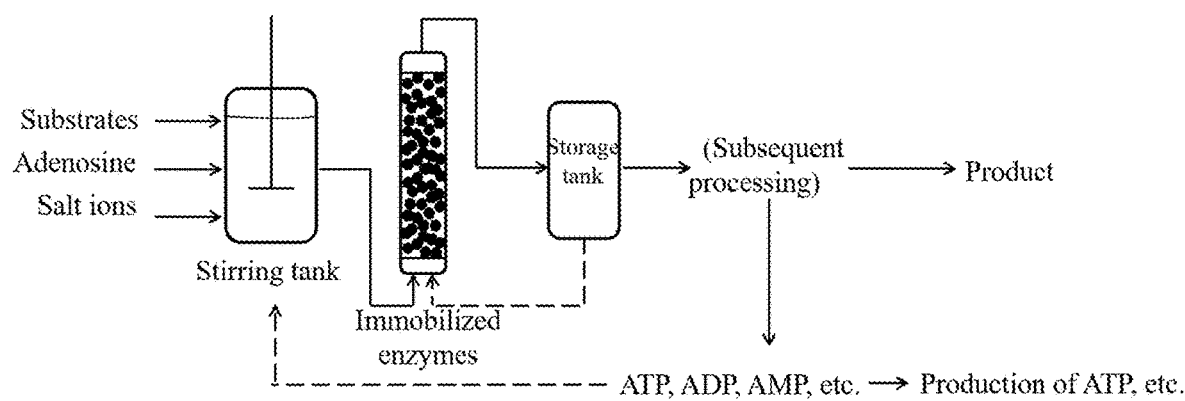
FIG. 3 is a flow chart showing the reaction process using immobilized enzymes according to the present invention.

Example 6 Production of Fructose 1,6-Diphosphate (Immobilized Enzyme) by an Enzymatic Method FIG. 3 is a flow chart showing the reaction process using immobilized enzymes according to the present invention. As shown in FIG. 3, the operating steps for preparing fructose 1,6-diphosphate by an immobilized enzyme method are as follows:

(1) Immobilization of Catalytic Enzymes, ATP Regeneration Enzymes and AK Enzymes:

the catalytic enzyme fructokinase (FK) and phosphofructokinase (PFK) were commercially available, and were immobilized with a commercial epoxy immobilization carrier LX1000EP together with the preliminarily purified ADK enzyme, PAP enzyme and AK enzyme in Example 1.

The FK, PFK, ADK, PAP and AK enzymes were mixed into a mixed enzyme solution according to an activity ratio of 2:2:1:1:1, and the AK enzyme activity in the enzyme solution was 2000 U/L. 2 kg of LX1000EP wet carrier was added to the constant temperature stirring reaction tank, and mixed with the above enzyme solution, and stirred at 150 rpm for 12 hours at a condition of 20° C. The carrier was collected by filtration and washed twice with 0.02 M potassium phosphate buffer (pH 8.0) to obtain an immobilized mixed enzyme.

(2) Production of Fructose 1,6-Diphosphate in the Reaction Column:

the reaction solution was formulated, each 100 L contained substrate 1.8 kg of fructose, and 0.3 kg of adenosine, 2.0 kg of sodium hexametaphosphate, 0.5 kg of ammonium chloride, 0.5 kg of sodium chloride, 0.5 kg of magnesium sulfate heptahydrate, 0.2 kg of manganese sulfate and 0.85 kg of disodium hydrogen phosphate, and the solution was uniformly stirred when formulated to prevent precipitation. The pH was adjusted to 6.8 and the temperature was raised to 35-40° C.

The enzyme reaction column was prepared by charging 10 kg of the mixed immobilized enzyme in the above step (1) into the reaction column and exhausting the bubbles. The reaction solution was slowly passed through the enzyme reaction column from bottom to top at a flow rate of 30 L/h using a constant flow pump, and the temperature was controlled at 37° C. during the reaction. After 6 hours of the reaction, the reaction solution was collected, and the production amount of fructose 1,6-diphosphate was detected to be 30 g/L.

After the immobilized enzyme was circularly reacted for more than 20 times or stored at −4° C. for more than one month, the enzyme activity was reduced by 10-15%, therefore a part of new enzymes was needed to be added or replaced in proportion.

Example 7 Production of Carnosine by an Enzymatic Method

As shown in FIG. 2, the operating steps for preparing carnosine by an enzymatic method while coupling the free ATP regeneration enzyme and AK enzyme are as follows:

(1) Reaction of Synthesizing Carnosine in a Reaction Tank:

in the reaction tank, 100 L of the reaction system was a solution containing substrate 1.8 kg of L-histidine, 1.0 kg of β-alanine, and 0.25 kg of adenosine, 1.0 kg of sodium polyphosphate, 0.3 kg of sodium chloride, 0.38 kg of potassium chloride, 1.0 kg of magnesium chloride hexahydrate, and 0.6 kg of disodium hydrogen phosphate, and the solution was uniformly stirred when formulated to prevent precipitation. The pH value was adjusted to 8.0, and 1000 U/L of carnosine synthetase and 600 U/L of ADK enzyme, 600 U/L of PAP enzyme, 800 U/L AK of enzyme were added to the reaction system to start the reaction. The pH value was controlled to 8.0 during the reaction and the temperature was 37° C.

After 6 hours of reaction, the production amount of carnosine was 21 g/L. The detection conditions of HPLC were as follows: Kromasil C18 chromatographic column (the same as that in Example 2), detection wavelength of 210 nm, and detection temperature of 25° C., the detection flow rate of 0.8 ml/min, and the mobile phase of an aqueous solution containing 80 mM phosphate buffer and 15% methanol.

(2) Separation of Carnosine Synthetase and ATP Regeneration Enzyme in a Filter:

The reaction solution in the reaction system of step (1) was passed through a filter to separate the carnosine synthetase, ATP regeneration enzyme and AK enzyme by an ultrafiltration method, and a membrane package (purchased from Pall Corporation, with a molecular weight cut off of 20 kDa) was placed in the filter, and the filtrate was a reaction solution containing carnosine, ATP, ADP, AMP and salts and the like after the enzyme was separated, and the filtrate can be further purified by ion exchange chromatography and the like.

The recovered carnosine synthetase, ADK enzyme, PAP enzyme and AK enzyme were detected to have an activity which is reduced by 10%-20% compared with that before the reaction, and can be used again for the reaction in step (1) after the corresponding new enzyme was added.

Example 8 Production of Theanine by an Enzymatic Method

As shown in FIG. 2, the operating steps for preparing theanine by an enzymatic method while coupling the free ATP regeneration enzyme and AK enzyme are as follows:

(1) Reaction of synthesizing theanine and regenerating ATP in the reaction tank:

in the reaction tank, 100 L of the reaction system was a solution containing substrate 1.5 kg of sodium glutamate, 0.7 kg of ethylamine hydrochloride, and 0.2 kg of adenosine, 2.0 kg of polyphoshoric acid, 1.0 kg of magnesium chloride hexahydrate, and 0.5 kg of disodium hydrogen phosphate, and the solution was uniformly stirred when formulated to prevent precipitation. The pH value was adjusted to 7.0, and 500 U/L of theanine synthetase and 500 U/L of PPK enzyme, 500 U/L of ADK enzyme, 800 U/L of AK enzyme were added to the reaction system to start the reaction. The pH value was controlled to 7.0 during the reaction and the temperature was 30° C.

After 5 hours of reaction, the production amount of theanine was 14 g/L. The detection conditions of HPLC were as follows: Kromasil C18 chromatographic column (the same as that in Example 2), detection wavelength of 203 nm, and detection temperature of 30° C., the detection flow rate of 1 ml/min, and the mobile phase of an aqueous solution containing 0.05% TFA and 5% acetonitrile.

(2) Separation of Theanine and ATP Regeneration Enzyme in a Filter:

the reaction solution in the reaction system of step (1) was passed through a filter to separate the theanine synthetase, ATP regeneration enzyme and AK enzyme by an ultrafiltration method, and a membrane package (purchased from Pall Corporation, with a molecular weight cut off of 20 kDa) was placed in the filter, and the filtrate was a reaction solution containing theanine, ATP, ADP, AMP and salts and the like after the enzyme was separated, and the filtrate can be further purified by ion exchange chromatography and the like.

The recovered theanine synthetase, PPK enzyme, ADK enzyme and AK enzyme were detected to have an activity which is reduced by 5%-10% compared with that before the reaction, and can be used again for the reaction in step (1) after the corresponding new enzyme was added.

Example 9 Production of Glutathione (Immobilized Enzyme) by an Enzymatic Method As shown in FIG. 3, the operating steps for preparing GSH by an immobilized enzymatic method are as follows:

(1) immobilization of enzyme: the GshF enzyme, PPK enzyme, PAP enzyme and AK enzyme for catalysis were immobilized with a commercial epoxy immobilization carrier LX1000EP.

The crude enzyme GshF enzyme 8000 U/L, PPK enzyme 2000 U/L, PAP enzyme 2000 U/L and AK enzyme 5000 U/L were mixed to formulate a mixed enzyme solution. The LX1000EP wet carrier was added to the constant temperature stirring reaction tank, and mixed with the above enzyme solution at a mass ratio of the immobilization carrier to the enzyme of 30:1, and stirred at 150 rpm for 12 hours at 20° C. The carrier was collected by filtration and washed twice with 0.02 M potassium phosphate buffer (pH 8.0) to obtain an immobilized mixed enzyme.

(2) Generation of Glutathione GSH in the Reaction Column:

the reaction solution was formulated, each 100 L of the reaction system was a solution containing substrate 3.5 kg of glutamic acid, 3.2 kg of cysteine and 3.3 kg of glycine, 0.5 kg of adenosine, and 3.0 kg of sodium hexametaphosphate, 0.3 kg of sodium chloride, 0.8 kg of magnesium chloride hexahydrate, and 0.6 kg of potassium dihydrogen phosphate, and the solution was uniformly stirred when formulated to prevent precipitation. The pH was adjusted to 7.5 and the temperature was raised to 37-40° C.

The enzyme reaction column was prepared by charging 20 kg of the mixed immobilized enzyme in step (1) into the reaction column apparatus and exhausting the bubbles. The reaction solution was slowly passed through the enzyme reaction column from bottom to top at a flow rate of 20 L/h using a constant flow pump, and the temperature was controlled at 37-40° C. during the reaction. After 6 hours of reaction, the reaction solution was collected, and the production amount of glutathione was detected by high performance liquid chromatography (HPLC) to be 40 g/L. The HPLC detection conditions were the same as those in step (1) of Example 3.

(3) A Continuous Reaction for Generating GSH in the Reaction Column, that is, a Continuous Reaction of Step (2):

the same reaction solution as described in step (2) was formulated, and continuously passed through the enzyme reaction column at a flow rate of 20 L/h from bottom to top, and the temperature during the reaction was controlled at 37 to 40° C.

After 6 hours of reaction, the production amount of GSH was detected by HPLC to be 40 g/L. The HPLC detection conditions were the same as those in step (1) of Example 3. In this step, the enzyme was recycled.

After the immobilized enzyme was circularly reacted for more than 20 times or stored at −4° C. for more than one month, the enzyme activity was reduced by 10%, therefore a part of new enzymes was needed to be added or replaced in proportion.

Example 10 Production of Creatine Phosphate by an Enzymatic Method

As shown in FIG. 2, the operating steps for preparing creatine phosphate by an enzymatic method while coupling the free ATP regeneration enzyme and AK enzyme are as follows:

(1) Reaction of Synthesizing Creatine Phosphate in a Reaction Tank:

In the reaction tank, 100 L of the reaction system was a solution containing substrate 0.2 kg of creatine, and 0.001 kg of adenosine, 0.47 kg of polyphoshoric acid, 0.053 kg of ammonium chloride, 0.2 kg of magnesium chloride hexahydrate, 0.072 kg of manganese chloride monohydrate and 1.2 kg of Tris, and the solution was uniformly stirred when formulated to prevent precipitation. The pH was adjusted to 10.0, and creatine kinase 1 U/L, PPK enzyme 0.01 U/L, ADK enzyme 0.01 U/L, PAP enzyme 0.01 U/L and AK enzyme 0.01 U/L were added to the reaction system to start the reaction. The pH value was controlled to 10.0 during the reaction and the temperature was 55° C.

After 5 hours of reaction, the production amount of creatine phosphate was detected by HPLC to be 2 g/L. The HPLC detection conditions were the same as those in step (1) of Example 2.

(2) Separation of Creatine Kinase, ATP Regeneration Enzyme and AK Enzyme in a Filter:

the reaction solution in the reaction system of step (1) was passed through a filter to separate the creatine kinase, ATP regeneration enzyme and AK enzyme by an ultrafiltration method, and a membrane package (purchased from Pall Corporation, with a molecular weight cut off of 20 kDa) was placed in the filter, and the filtrate was a reaction solution containing creatine phosphate, ATP, ADP, AMP and salts and the like after the enzyme was separated, and the filtrate can be further purified by ion exchange chromatography and the like.

The recovered creatine kinase, PPK enzyme, ADK enzyme, PAP enzyme and AK enzyme were detected to have an activity which is reduced by 30%-50% compared with that before the reaction, and can be used again for the reaction in step (1) after the corresponding new enzyme was added.

Example 11 Production of S-Adenosylmethionine by an Enzymatic Method

As shown in FIG. 2, the operating steps for preparing SAM by an enzymatic method while coupling the free ATP regeneration enzyme and AK enzyme are as follows:

(1) Generation of SAM in the Reaction Tank:

In the reaction tank, 100 L of the reaction system was a solution containing substrate 3.0 kg of methionine, 5.0 kg of adenosine, and 14.1 kg of polyphosphoric acid, 3.73 kg of sodium chloride, 4.07 kg of magnesium chloride hexahydrate, and 1.56 kg of sodium dihydrogen phosphate dihydrate, and the solution was uniformly stirred when formulated to prevent precipitation. The pH was adjusted to 5.0, and MAT enzyme 8000 U/L, PPK enzyme 2500 U/L, ADK enzyme 2500 U/L, PAP enzyme 2500 U/L and AK enzyme 3000 U/L were added to the reaction system to start the reaction, and the enzymes added were all crude enzyme solutions. The pH value was controlled to 5.0 during the reaction and the temperature was 50° C.

After 8 hours of reaction, the production amount of SAM was detected by high performance liquid chromatography (HPLC) to be 25 g/L. The HPLC detection conditions were the same as those in step (1) of Example 5.

(2) Separation of the Enzyme in the Filter:

the reaction solution of the step (1) was passed through a filter to separate the mixed enzyme by an ultrafiltration method, and a membrane package (purchased from Pall Corporation, with a molecular weight cut off of 20 kDa) was placed in the filter, and the filtrate was a reaction solution containing SAM, ATP, ADP, AMP and salts and the like after the enzyme was separated, and the filtrate can be further purified by ion exchange chromatography and the like.

The enzyme separated in step (2) was added to the reaction tank through a reflux port of the filter, and a new enzyme having a concentration of 15-30% of the original enzyme was added for the reaction. The reaction solution was formulated in the same manner as in the above step (1).

The continuous reaction for producing SAM was carried out under the conditions of a pH 5.0 at 50° C.; after 8 hours, the production amount of SAM detected by HPLC was 25 g/L. The HPLC detection conditions were the same as those in the above step (1). In this step, the enzyme was recycled.

Example 12 Production of Glutathione by an Enzymatic Method

As shown in FIG. 2, the operating steps for preparing GSH by an enzymatic method while coupling the free ATP regeneration enzyme and AK enzyme are as follows:

(1) Generation of GSH in the Reaction Tank:

in the reaction tank, 100 L of the reaction system was a solution containing substrate 0.1 kg of glutamic acid, 0.1 kg of cysteine and 0.05 kg of glycine, 0.001 kg of adenosine, and 0.47 kg of polyphoshoric acid, 0.066 kg of ammonium sulfate, 0.074 kg of potassium chloride, 0.2 kg of magnesium chloride hexahydrate, and 0.12 kg of Tris, and the solution was uniformly stirred when formulated to prevent precipitation. The pH was adjusted to 10.0, and GshF enzyme 0.01 U/L, PPK enzyme 0.01 U/L, ADK enzyme 0.01 U/L, PAP enzyme 0.01 U/L and AK enzyme 0.01 U/L were added to the reaction system to start the reaction, and the enzymes added were all crude enzyme solutions. The pH value was controlled to 10.0 during the reaction and the temperature was 25° C.

After 8 hours of reaction, the production amount of glutathione was detected by high performance liquid chromatography (HPLC) to be 0.6 g/L. The HPLC detection conditions were the same as those in step (1) of Example 3.

(2) Separation of the Enzyme in the Filter:

the reaction solution of the step (1) was passed through a filter to separate the mixed enzyme by an ultrafiltration method, and a membrane package (purchased from Pall Corporation, with a molecular weight cut off of 20 kDa) was placed in the filter, and the filtrate was a reaction solution containing GSH, ATP, ADP, AMP and salts and the like after the enzyme was separated, and the filtrate can be further purified by ion exchange chromatography and the like.

The enzyme separated in step (2) was added to the reaction tank through a reflux port of the filter, and a new enzyme having a concentration of 30-50% of the original enzyme was added for the reaction. The reaction solution was formulated in the same manner as in the above step (1).

The continuous reaction for producing GSH was carried out under the conditions of a pH 10.0 at 25° C.; after 8 hours, the production amount of GSH detected by HPLC was 0.6 g/L.

Example 13 Production of Fructose 1,6-Diphosphate (Immobilized Enzyme) by an Enzymatic Method As shown in FIG. 3, the operating steps for preparing fructose 1,6-diphosphate by an enzymatic method while coupling the ATP regeneration enzyme and AK enzyme are as follows:

(1) Immobilization of Catalytic Enzymes, ATP Regeneration Enzymes and AK Enzymes:

the catalytic enzyme fructokinase (FK) and phosphofructokinase (PFK) were commercially available, and were immobilized with a commercial epoxy immobilization carrier LX1000EP or amino-containing synthetic polymer carrier LX1000HA together with the preliminarily purified ATP regeneration enzyme PPK enzyme and PAP enzyme in Example 1, respectively.

FK, PFK, PPK, PAP and AK enzymes were respectively made into enzyme solution, each of 3 L, activities of FK, PFK and AK enzymes were all 8000 U/L, and activities of PPK and PAP enzymes were 5000 U/L.

1 kg of LX1000EP wet carrier was added to the constant temperature stirring reaction tank, and mixed with 3 L of FK enzyme solution, and stirred at 150 rpm for 12 hours at a condition of 20° C. The carrier was collected by filtration and washed twice with 0.02 M potassium phosphate buffer (pH 8.0) to obtain an immobilized FK enzyme. The PFK enzyme was immobilized in the same manner.

1 kg of LX1000HA wet carrier was added to the constant temperature stirring reaction tank, and mixed with the 3 L of the above PPK enzyme solution, and stirred at 150 rpm for 12 hours at a condition of 20° C. The carrier was collected by filtration and washed twice with 0.02 M potassium phosphate buffer (pH 8.0) to obtain an immobilized PPK enzyme. The PAP and AK enzymes were immobilized in the same manner.

(2) Production of Fructose 1,6-Diphosphate in the Reaction Column:

the reaction solution was formulated, each 100 L contained substrate 3.6 kg of fructose, and 2.0 kg of adenosine, 8.0 kg of sodium hexametaphosphate, 1.6 kg of ammonium chloride, 4.0 kg of magnesium chloride hexahydrate, and 1.56 kg of sodium dihydrogen phosphate dihydrate, and the solution was uniformly stirred when formulated to prevent precipitation. The pH was adjusted to 6.0 and the temperature was raised to 50° C.

The enzyme reaction column was prepared by charging 10 kg of the mixed immobilized enzyme in the above step (1) into the reaction column and exhausting the bubbles. The reaction solution was slowly passed through the enzyme reaction column from bottom to top at a flow rate of 30 L/h using a constant flow pump, and the temperature was controlled at 50° C. during the reaction. After 6 hours of the circular reaction, the reaction solution was collected, and the production amount of fructose 1,6-diphosphate was detected by HPLC to be 25 g/L.

After the immobilized enzyme was circularly reacted for more than 20 times or stored at −4° C. for more than one month, the enzyme activity was reduced by 20-40%, therefore a part of new enzymes was needed to be added or replaced in proportion.

Example 14 Production of S-Adenosylmethionine (Immobilized Enzyme) by an Enzymatic Method As shown in FIG. 3, the operating steps for preparing SAM by an enzymatic method while coupling the ATP regeneration enzyme and AK enzyme are as follows:

(1) Immobilization of the Enzyme

The MAT enzyme, PPK enzyme, ADK enzyme, PAP enzyme and AK enzyme for catalysis were immobilized with a commercial amino-containing synthetic polymer carrier LX1000HA.

The crude enzyme MAT enzyme 12000 U/L was added with 2 kg of LX1000HA wet carrier in a constant temperature stirring reaction tank, and stirred at 150 rpm for 12 hours at 20° C. The carrier was collected by filtration and washed twice with 0.02 M potassium phosphate buffer (pH 8.0) to obtain an immobilized MAT enzyme. 5000 U/L of PPK enzyme, 5000 U/L of ADK enzyme, 5000 U/L of PAP enzyme, and 8000 U/L of AK enzyme were separately immobilized on the LX1000HA carrier in the same manner.

(2) Generation of SAM in the Reaction Column:

the reaction solution was formulated, each 100 L contained a solution containing substrate 3.0 kg of methionine, 5.0 kg of adenosine, and 18.36 kg of sodium hexametaphosphate, 3.73 kg of potassium chloride, 2.16 kg of manganese chloride, and 1.56 kg of sodium dihydrogen phosphate dihydrate, and the solution was uniformly stirred when formulated to prevent precipitation. The pH was adjusted to 6.0 and the temperature was raised to 55° C.

The enzyme reaction column was prepared by charging 20 kg of the immobilized enzyme in step (1) into the reaction column apparatus and exhausting the bubbles. The reaction solution was slowly passed through the enzyme reaction column from bottom to top at a flow rate of 20 L/h using a constant flow pump, and the temperature was controlled at 55° C. during the reaction. After 8 hours of reaction, the reaction solution was collected, and the production amount of SAM was detected by high performance liquid chromatography (HPLC) to be 27 g/L. The HPLC detection conditions were the same as those in step (1) of Example 5.

(3) A Continuous Reaction for Generating SAM in the Reaction Column, that is, a Continuous Reaction of the Step (2):

the same reaction solution as described in step (2) was formulated, and continuously passed through the enzyme reaction column at a flow rate of 20 L/h from bottom to top, and the temperature during the reaction was controlled at 55° C.

After 8 hours of reaction, the production amount of SAM was detected by HPLC to be 27 g/L. The HPLC detection conditions were the same as those in step (1) of Example 5. In this step, the enzyme was recycled.

After the immobilized enzyme was circularly reacted for more than 20 times or stored at −4° C. for more than one month, the enzyme activity was reduced by 30%, therefore a part of new enzymes was needed to be added or replaced in proportion.

Example 15

The reaction was scaled up in tons, in the reaction tank, 1000 L of the reaction system was a solution containing substrate 25.0 kg of glutamic acid, 25.0 kg of cysteine and 15.0 kg of glycine, 5.0 kg of adenosine, and 25.0 kg of sodium hexametaphosphate, 10.0 kg of ammonium sulfate, 5.2 kg of magnesium chloride hexahydrate, and 1.0 kg of manganese chloride monohydrate, and the solution was uniformly stirred when formulated to prevent precipitation. The pH was adjusted to 7.0, and GshF enzyme 1000 U/L, PPK enzyme 500 U/L, ADK enzyme 500 U/L, PAP enzyme 500 U/L and AK enzyme 750 U/L were added to the reaction system to start the reaction, and the enzymes added were all crude enzyme solutions. The pH value was controlled to 7.0 during the reaction and the temperature was 37° C.

After 6 hours of reaction, the production amount of glutathione was detected by high performance liquid chromatography (HPLC) to be 36.4 g/L, and the HPLC detection conditions were the same as those in step (1) of Example 3.

(2) Separation of the Enzymes Using an Ultrafiltration Apparatus

The reaction solution from step (1) was filtered using an ultrafiltration apparatus, and the interception size of the ultrafiltration membrane was 5 kDa, and the filtrate and the retentate were separately collected. The filtrate was a reaction solution containing the product after separation of the enzyme, and the retentate was a recovered enzyme solution.

(3) The retentate from step (2) was added to the reaction tank, and new enzyme in an amount of 5-10% of the original enzyme was added to carry out the reaction. The reaction solution was formulated in the same manner as in the above step (1). After 6 hours of reaction, the production amount of glutathione was detected by high performance liquid chromatography (HPLC) to be 36.3 g/L, and the HPLC detection conditions were the same as those in step (1) of Example 3. In this step, the enzyme was recycled.

Example 16 Production of GSH by an Enzymatic Method

The reaction was scaled up in tons, in the reaction tank, 1000 L of the reaction system was a solution containing substrate 5.0 kg of glutamic acid, 5.0 kg of cysteine and 5.0 kg of glycine, 5.0 kg of adenosine, and 25.0 kg of sodium hexametaphosphate, 10.0 kg of ammonium sulfate, 5.2 kg of magnesium chloride hexahydrate, and 1.0 kg of manganese chloride monohydrate, and the solution was uniformly stirred when formulated to prevent precipitation. The pH was adjusted to 7.0, and GshF enzyme 1000 U/L, ADK enzyme 500 U/L, PAP enzyme 500 U/L and AK enzyme 750 U/L were added to the reaction system to start the reaction, and the enzymes added were all crude enzyme solutions. After the reaction started, the amino acid solution was supplemented. The solution contained 20.0 kg of glutamic acid, 20.0 kg of cysteine and 10.0 kg of glycine, the supplementary rate was controlled to be completed within 6 hours, the pH value was controlled to 7.0 during the reaction, and the temperature was 37° C.

After 8 hours of reaction, the production amount of glutathione was detected by high performance liquid chromatography (HPLC) to be 37 g/L, and the HPLC detection conditions were the same as those in step (1) of Example 3.

(2) Separation of the Enzymes Using an Ultrafiltration Apparatus the reaction solution from step (1) was filtered using an ultrafiltration apparatus, the interception size of the ultrafiltration membrane was 5 kDa, and the filtrate and the retentate were separately collected. The filtrate was a reaction solution containing the product after separation of the enzyme, and the retentate was a recovered enzyme solution.

(3) The retentate from step (2) was added to the reaction tank, and new enzyme in an amount of 5-10% of the original enzyme was added to carry out the reaction. The reaction solution was formulated in the same manner as in the above step (1). After 8 hours of reaction, the production amount of glutathione was detected by high performance liquid chromatography (HPLC) to be 37 g/L, and the HPLC detection conditions were the same as those in step (1) of Example 3. In this step, the enzyme was recycled.

Example 17 Cell-Free Protein Expression of GshF Enzyme

The operating steps for the cell-free protein expression of the GshF enzyme and coupling of the ATP regeneration enzyme and the AK enzyme are as follows:

(1) Construction of Expression Vector pIVEX2.4d-gshF:

According to the sequence of the gshF gene, a pair of amplification primers were designed, and the primer sequences were as follows:

```
gshF sense primer:
5'-CCATGGCATTAAACCAACTTCTTCAAAAACTG-3';
and gshF antisense primer:
5'-CGGATCCTTAAGTTTGACCAGCCACTATTTC-3';
```

The DNA of *Streptococcus thermophilus* strain was extracted and used as a template to amplify the gshF gene fragment by PCR, double digested with Nco I and BamH I, and then ligated into pIVEX2.4d vector (purchased from Roche Corporation). The pIVEX2.4d-gshF vector was constructed and sequenced to be correct.

(2) Preparation of Cell-Free Extract of *E. coli*

The *E. coli* A19 (deletion nuclease I gene, non-degraded exogenous gene) monoclone was inoculated into LB medium, cultured to logarithmic growth phase, and then inoculated into a fermentor containing 5 L of fermentation medium, and cultured until $OD_{600}$ reached 3, at this time the bacteria were harvested by centrifugation. For components of LB medium and fermentation medium, please refer to Example 1.

The bacteria were resuspended in S30 buffer, washed for three times at 4° C., and the bacteria were collected and stored at −80° C. The components of S30 buffer were: 14 mM of magnesium acetate, 60 mM of potassium acetate, 1 mM of dithiothreitol (DTT), and 10 mM of Tris (pH 8.1).

The weight of the bacteria was measured and redissolved with 100 ml of S30 buffer per 10 g of the bacteria, meanwhile, 1 mM DTT was added. The bacteria were homogenized and disrupted under high pressure at 75 kPa, then 1 mM DTT was added, and the supernatant was collected by centrifugation at 4° C. Cell-free extracts of E. coli were prepared by incubating at 100 rpm, 37° C. for 30 minutes in a constant temperature shaker.

(3) Expression of Protein Using Cell-Free Extract and Coupling of ATP Regeneration Enzyme and AK Enzyme In a 100 μl protein expression system, 20 μl of the cell-free extract of E. coli from step (2) was added, 15 μg/ml of the expression vector pIVEX2.4d-gshF from step (1) was added, and 15 mM of magnesium acetate, 50 mM of ammonium acetate, 50 mM of HEPES-potassium hydroxide (pH 7.5), 2% of PEG 8000, 2 mM of DTT, 0.33 mM of NAD$^+$, 0.27 mM of coenzyme A, 4 mM of oxalic acid, 1 U/μl of T7 RNA polymerase, 2 mM of adenosine, 1 mM of GTP, 1 mM of CTP, 1 mM of UTP, and 2 mM of each of 20 amino acids were added, meanwhile, 1 U/μl of PPK, 1 U/μl of ADK, 1 U/μl of AK, and 10 mM of sodium polyphosphate were added and used to produce and regenerate ATP. The reaction was carried out for 6 hours at 200 rpm and 30° C. in a constant temperature shaker.

system to start the reaction. The pH value was controlled to 7.0 during the reaction and the temperature was 35° C.

After 6 hours of reaction, the production amount of creatine phosphate was 25 g/L, and 90% or more of ATP was converted into ADP and AMP. The HPLC detection conditions were the same as those in step (1) of Example 2.

Compared with Example 2, it can be seen that adenosine is used instead of ATP, and AK enzyme and ATP regeneration enzyme are added for enzymatic reaction. Although the amount of enzyme required for the reaction is generally increased, the usage amount of adenosine is small and the price is low, thereby greatly reducing the cost of industrial production. A small amount of by-products ATP, ADP and AMP can be either directly used for the cyclic reaction, or for the production of ATP, thereby having certain economic benefits and being more suitable for industrial mass production.

At the same time, the ATP regeneration system described in the present invention can also be applied to various enzymatic reactions requiring ATP.

Although the present invention has been disclosed in the above embodiments, the above embodiments are not intended to limit the present invention, and various selections and modifications can be made without departing from the spirit and scope of the present invention by any person skilled in the art. Therefore, the protection scope of the present invention is defined by the claims and their equivalents.

SEQUENCE LISTING

```
<160> NUMBER OF SEQ ID NOS: 2

<210> SEQ ID NO 1
<211> LENGTH: 32
<212> TYPE: DNA
<213> ORGANISM: Streptococcus thermophilus

<400> SEQUENCE: 1
ccatggcatt aaaccaactt cttcaaaaac tg                              32

<210> SEQ ID NO 2
<211> LENGTH: 31
<212> TYPE: DNA
<213> ORGANISM: Streptococcus thermophilus

<400> SEQUENCE: 2
cggatcctta agtttgacca gccactattt c                              31
```

Figure 5:
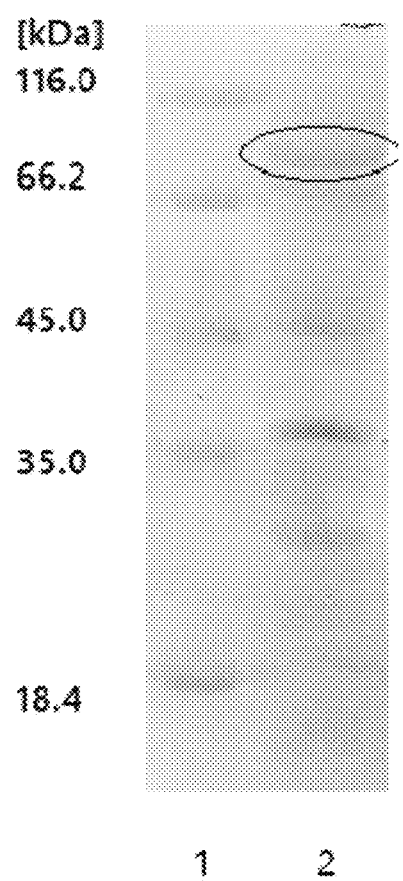
FIG. 5 is an SDS-PAGE diagram of the expression of gshF enzyme using cell-free extracts according to the present invention.

FIG. 5 is an SDS-PAGE diagram of the expression of gshF enzyme using cell-free extracts, as shown in FIG. 5: Lane 1 is a protein marker 14.4-116 kDa; Lane 2 is a cell-free expression of gshF enzyme, 85 kDa.

Comparative Example 1 Production of Creatine Phosphate by an Enzymatic Method

The operating steps for preparing creatine phosphate by an enzymatic method are as follows:

In the reaction tank, 100 L of the reaction system was a solution containing substrate 2.0 kg of creatine, and 8.0 kg of ATP, 0.4 kg of potassium chloride, 0.5 kg of magnesium chloride hexahydrate, and 0.3 kg of disodium hydrogen phosphate, and the solution was uniformly stirred when formulated to prevent precipitation. The pH was adjusted to 7.0, and 1000 U/L creatine kinase was added to the reaction

What is claimed is:

1. A method of producing a product from an enzymatic reaction requiring adenosine triphosphate (ATP), the method comprising the following steps:

(1) adding ATP regeneration enzymes, AK (adenosine kinase) enzyme, enzyme that produces the product, and adenosine to an enzymatic reaction system to carry out the enzymatic reaction, wherein:

the ATP generation enzymes are a combination of two or three enzymes selected from the group consisting of: polyphosphate kinase (PPK), adenylate kinase (ADK), and polyphosphate: AMP phosphotransferase (PAP);

adenosine is used instead of ATP and adenosine monophosphate (AMP);

the product is creatine phosphate;

the enzyme that the produces the product is a transferase for transferring a phosphate group and is creatine kinase;
the enzymatic reaction requiring ATP is a synthesis reaction of creatine phosphate; and
the enzymatic reaction system is a 100 L enzymatic reaction system that comprises:
a solution comprising:
2.0 kg of creatine;
0.2 kg of adenosine;
1.8 kg of sodium polyphosphate;
0.4 kg of potassium chloride;
0.5 kg of magnesium chloride hexahydrate; and
0.3 kg of disodium hydrogen phosphate, wherein the pH of the solution is adjusted to 7.0;
ATP regeneration enzymes comprising PPK enzyme 500 U/L and ADK enzyme 500 U/L;
AK enzyme 500 U/L; and
creatine kinase 1000 U/L;
wherein the enzymatic reaction system is maintained at a temperature of 35° C. and a pH of 7.0;
(2) separating the ATP regeneration enzymes, the AK enzyme, and the creatine kinase from the enzymatic reaction system after five hours of reacting the solution, the ATP regeneration enzymes, the AK enzyme, and the creatine kinase to produce a filtrate comprising creatine phosphate, ATP, ADP, and AMP, wherein:
the ATP regeneration enzymes, the AK enzyme, and the creatine kinase are separated from the enzymatic reaction system with an ultrafiltration membrane in a filter;
enzyme activity of the separated ATP regeneration enzymes, the AK enzyme, and the creatine kinase are reduced by 5%-20% compared with that before enzymatic reaction; and
the separated ATP regeneration enzymes, the AK enzyme, and the creatine kinase are recycled for use in step (1) for the enzymatic reaction; and
(3) separating and purifying the filtrate of step (2) to obtain the creatine phosphate.

2. A method of producing a product from an enzymatic reaction requiring adenosine triphosphate (ATP), the method comprising the following steps:
(1) adding ATP regeneration enzymes, AK (adenosine kinase) enzyme, enzyme that produces the product, and adenosine to an enzymatic reaction system to carry out the enzymatic reaction, wherein:
the ATP generation enzymes are a combination of two or three enzymes selected from the group consisting of: polyphosphate kinase (PPK), adenylate kinase (ADK), and polyphosphate: AMP phosphotransferase (PAP);
adenosine is used instead of ATP and adenosine monophosphate (AMP);
the product is fructose 1,6-diphosphate;
the enzyme that produces the product is a transferase for transferring a phosphate group selected from fructokinase (FK) and phosphofructokinase (PFK);
the enzymatic reaction requiring ATP is a synthesis reaction of fructose 1,6-diphosphate; and
the enzymatic reaction system is a 100 L enzymatic reaction system that comprises a reaction solution comprising:
1.8 kg of fructose;
0.3 kg of adenosine;
2.0 kg of sodium hexametaphosphate;
0.5 kg of ammonium chloride;
0.5 kg of sodium chloride;
0.5 kg of magnesium sulfate heptahydrate;
0.2 kg of manganese sulfate; and
0.85 kg of disodium hydrogen phosphate,
wherein the pH of the reaction solution is adjusted to 6.8 and brought to a temperature of 35-40° C.;
the ATP regeneration enzymes, the AK enzyme, and catalytic enzymes are immobilized in the enzymatic reaction system;
the ATP generation enzymes are a combination of the ADK enzyme and the PAP enzyme;
the catalytic enzymes are fructokinase (FK) and phosphofructokinase (PFK);
the FK enzyme, the PFK enzyme, the ADK enzyme, the PAP enzyme, and the AK enzyme in the enzymatic reaction system are in an activity ratio of 2:2:1:1:1;
the AK enzyme activity in the enzyme solution is 2000 U/L;
the reaction solution is passed through the enzymatic reaction system at a constant flow rate of 30 L/h; and
the enzymatic reaction system is maintained at 37° C. for the synthesis of fructose 1,6-diphosphate;
(2) directly separating the ATP regeneration enzymes, the AK enzyme, the FK enzyme, and the PFK enzyme from the enzymatic reaction system to produce a filtrate comprising fructose 1,6-diphosphate, ATP, ADP, and AMP; and
(3) separating and purifying the filtrate of step (2) to obtain the fructose 1,6-diphosphate.

3. A method of producing a product from an enzymatic reaction requiring adenosine triphosphate (ATP), the method comprising the following steps:
(1) adding ATP regeneration enzymes, AK (adenosine kinase) enzyme, enzyme that produces the product, and adenosine to an enzymatic reaction system to carry out the enzymatic reaction, wherein:
the ATP generation enzymes are a combination of two or three enzymes selected from the group consisting of: polyphosphate kinase (PPK), adenylate kinase (ADK), and polyphosphate: AMP phosphotransferase (PAP);
adenosine is used instead of ATP and adenosine monophosphate (AMP);
the product is carnosine;
the enzyme that the produces the product is a transferase for transferring a phosphate group and is carnosine synthetase;
the enzymatic reaction requiring ATP is a synthesis reaction of carnosine; and
the enzymatic reaction system is a 100 L enzymatic reaction system that comprises:
a solution comprising:
1.8 kg of L-histidine;
1.0 kg of β-alanine;
0.25 kg of adenosine;
1.0 kg of sodium polyphosphate;
0.3 kg of sodium chloride;
0.38 kg of potassium chloride;
1.0 kg of magnesium chloride hexahydrate; and
0.6 kg of disodium hydrogen phosphate, wherein the pH of the solution is adjusted to 8.0;
ATP regeneration enzymes comprising:
ADK enzyme 600 U/L; and
PAP enzyme 600 U/L;
AK enzyme 800 U/L; and carnosine synthetase 1000 U/L;
   wherein the enzymatic reaction system is maintained at a temperature of 37° C. and a pH of 8.0;
(2) separating the ATP regeneration enzymes, the AK enzyme, and the carnosine synthetase from the enzymatic reaction system to produce a filtrate comprising carnosine, ATP, ADP, and AMP, wherein:
   the ATP regeneration enzymes, the AK enzyme, and the carnosine synthase are separated from the enzymatic reaction system with an ultrafiltration membrane in a filter;
   the activity of the separated ATP regeneration enzymes, the separated AK enzyme, and the separated carnosine synthase are reduced by 10%-20% compared with that before the reaction; and
   the separated ATP regeneration enzyme, the separated AK enzyme, and the separated carnosine synthase are recycled for use in step (1) for the enzymatic reaction; and
(3) separating and purifying the filtrate of step (2) to obtain the carnosine.

4. A method of producing a product from an enzymatic reaction requiring adenosine triphosphate (ATP), the method comprising the following steps:
(1) adding ATP regeneration enzymes, AK (adenosine kinase) enzyme, enzyme that produces the product, and adenosine to an enzymatic reaction system to carry out the enzymatic reaction, wherein:
   the ATP generation enzymes are a combination of two or three enzymes selected from the group consisting of: polyphosphate kinase (PPK), adenylate kinase (ADK), and polyphosphate: AMP phosphotransferase (PAP);
   adenosine is used instead of ATP and adenosine monophosphate (AMP);
   the product is theanine;
   the enzyme that the produces the product is a transferase for transferring a phosphate group and is theanine synthetase;
   the enzymatic reaction requiring ATP is a synthesis reaction of theanine; and
   the enzymatic reaction system is a 100 L enzymatic reaction system that comprises:
      a solution comprising:
         1.5 kg of sodium glutamate;
         0.7 kg of ethylamine hydrochloride;
         0.2 kg of adenosine;
         2.0 kg of polyphoshoric acid;
         1.0 kg of magnesium chloride hexahydrate, and
         0.5 kg of disodium hydrogen phosphate, wherein the pH of the solution is adjusted to 8.0;
      ATP regeneration enzymes comprising:
         PPK enzyme 500 U/L; and
         ADK enzyme 500 U/L;
      AK enzyme 800 U/L; and
      theanine synthetase 500 U/L;
      wherein the enzymatic reaction system is maintained at a temperature of 30° C. and a pH of 7.0;
(2) separating the ATP regeneration enzymes, the AK enzyme, and the theanine synthetase from the enzymatic reaction system to produce a filtrate comprising theanine, ATP, ADP, and AMP, wherein:
   the ATP regeneration enzymes, AK enzyme, and the theanine synthase are separated from the enzymatic reaction system with the ultrafiltration membrane in a filter;
   the activity of the separated ATP regeneration enzymes, the separated AK enzyme, and the separated theanine synthase are reduced by 5%-10% compared with that before the reaction; and
   the separated ATP regeneration enzymes the separated AK enzyme, and the separated theanine synthase are recycled for use in step (1) for the enzymatic reaction; and
(3) separating and purifying the filtrate of step (2) to obtain the theanine.

* * * * *